United States Patent [19]

Tenud et al.

[11] Patent Number: 4,801,750
[45] Date of Patent: Jan. 31, 1989

[54] PROCESS FOR THE PRODUCITON OF 2-CHLOROACETOACETIC ACID AMIDES

[75] Inventors: Leander Tenud, Visp, Switzerland; Raimund Miller, Hackensack, N.J.; Barry Jackson, Visp, Switzerland

[73] Assignee: Lonza Ltd., Gampel/Valais, Switzerland

[21] Appl. No.: 361,333

[22] Filed: Mar. 24, 1982

[30] Foreign Application Priority Data

Mar. 26, 1981 [CH] Switzerland ............ 2044/81
Sep. 17, 1981 [CH] Switzerland ............ 6004/81

[51] Int. Cl.⁴ .................................. C07C 102/06
[52] U.S. Cl. ........................ 564/199; 260/544 C; 260/544 Y; 564/136
[58] Field of Search ................ 564/199, 136; 260/45 TY

[56] References Cited

U.S. PATENT DOCUMENTS

| | | | |
|---|---|---|---|
| 3,249,499 | 5/1966 | Schmeling et al. | 260/ |
| 3,284,500 | 11/1966 | Tieman | 564/199 |
| 3,352,351 | 12/1974 | Scharpf | 260/ |
| 3,393,202 | 7/1968 | Kulka et al. | 260/ |
| 3,449,421 | 6/1969 | Pearson | 564/199 |
| 3,852,351 | 12/1974 | Scharpf | 564/200 |
| 4,093,654 | 6/1978 | Coffen | 564/198 |
| 4,214,002 | 7/1980 | Brandman et al. | 424/300 |

FOREIGN PATENT DOCUMENTS

| | | | |
|---|---|---|---|
| 0005849 | 12/1979 | European Pat. Off. | 564/200 |
| 0037015 | 10/1981 | European Pat. Off. | 564/200 |
| 1931964 | 7/1968 | Fed. Rep. of Germany | 564/200 |
| 782773 | 9/1957 | United Kingdom | 564/200 |

OTHER PUBLICATIONS

Rodd, "Chemistry of Carbon Compounds", vol. 1, Part B, Aliphatic Compounds, p. 874 (1952).
Wagner et al., "Synthetic Organic Chemistry", pp. 100–103 (1963).
Hurd et al., "Jour. American Chem. Soc.", vol. 62, No. 6, pp. 1548–1549 (1940).

Primary Examiner—Robert V. Hines
Attorney, Agent, or Firm—Fisher, Christen & Sabol

[57] ABSTRACT

Process for the production of 2-chloroacetoacetic acid amides. Diketene is converted at a temperature of +30° to −40° C. with the help of hydrogen chloride into acetoacetic acid chloride. Chlorine is introduced into the mixture at a temperature of +30° to −40° C., whereby 2-chloroacetoacetic acid chloride is formed. The latter is converted into the corresponding amide at a temperature of +50° to −40° C. by reaction with a N-compound having the formula:

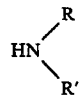

wherein
(i) R=R′=H, or
(ii) R=R′=alkyl, substituted alkyl, aryl, substituted aryl, alkyl aryl, substituted alkyl aryl, alkoxy aryl, substituted alkoxy aryl, alkoxy alkyl or substituted alkoxy alky, or
(iii) R=H, and R′=alkyl, substituted alkyl, aryl, substituted aryl, alkyl aryl, substituted alkyl aryl, alkoxy aryl, substituted alkoxy aryl, alkoxy alkyl or substituted alkoxy alkyl.

21 Claims, No Drawings

PROCESS FOR THE PRODUCITON OF 2-CHLOROACETOACETIC ACID AMIDES

BACKGROUND OF THE INVENTION

1. Field of This Invention

This invention relates to a process for the production of 2-chloroacetoacetic acid amides.

2. Prior Art

In the instance of known production processes known hitherto, one starts out with the corresponding substituted acetoacetic acid amides, such as, acetoacetic anilide, which are chlorinated either with chlorine gas or with sulfuryl chloride in solution or suspension. The chlorination of acetoacetic acid amides, as is well known, only has a slight selectivity. The crude yield of 2-chloroacetoacetic acid anilide from acetoacetic acid anilide is stated in U.S. Pat. No. 3,852,351 as being 76 percent; such anilide is stated as having a melting range of 122° to 135° C. (melting point in the literature is 138° C.). Chlorination with sulfuryl chloride is more selective and produces a pure end product having a melting point of 136° to 138° C. (see U.S. Pat. Nos. 3,249,499 and 3,393,202). However, the gases $SO_2$ and HCl, which develop during the reaction, are separated and the $SO_2$ must again be converted with chlorine into sulfuryl chloride.

BROAD DESCRIPTION OF THIS INVENTION

An object of this invention is to provide a simple, efficient and productive process for the production of 2-chloroacetoacetic acid amides. Other objects and advantages of this invention are set out herein or are obvious herefrom to one ordinarily skilled in the art.

The process of this invention achieves the objects and advantages of this invention.

The process of this invention involves a process for the production of a 2-chloroacetoacetic acid amide. Diketene is converted at a temperature of +30° to −40° C. with the help of hydrogen chloride into acetoacetic acid chloride. Then, by introducing chlorine into the solution at a temperature of +30° to −40° C., 2-chloroacetoacetic acid chloride is formed. The latter compound is converted at a temperature of +50° to −40° C. into the corresponding amide by reaction with N-containing compounds having the formula:

wherein (i) R and R' are H, or (ii) R and R' are the same or different alkyl, substituted alkyl, aryl, substituted aryl, alkyl aryl, substituted alkyl, aryl, alkoxy aryl, substituted alkoxy aryl, alkoxy alkyl or substituted alkoxy alkyl, or (iii) R is H, and R is alkyl, substituted alkyl, aryl, substituted aryl, alkyl aryl, substituted alkyl aryl, alkoxy aryl, substituted alkoxy aryl, alkoxy alkyl or substituted alkoxy alkyl.

2-Chloroacetoacetic acid amides are important intermediate products for the production of pesticides and herbicides. For example, the fungicide Vitavax ® of Uniroyal Inc. is derived from 2-chloroacetoacetic acid anilide.

DETAILED DESCRIPTION OF THIS INVENTION

Diketene is converted at a temperature of +30° to −40° C. with HCl into the acetoacetic acid chloride. 2-Chloroacetoacetic acid chloride is then formed by introduction of chlorine at a temperature of +30° to −40° C. The chloride is converted by the addition of 1 mole of the corresponding amine and 1 mole of tertiary base, such as triethylamine, or 2 moles of the corresponding amine into the corresponding 2-chloroacetoacetic acid amine.

The chlorination, in both chlorination steps, can be carried out in the presence of an acid catalyst (or catalysts), such as, a Lewis acid, for example, $PCl_3$ or $FeCl_3$, an inorganic acid, for example, sulfuric acid or perchloric acid, or a strong organic carboxylic acid, for example, acetic acid trifluoroacetic acid or p-toluene sulfonic acid. Combinations of acid catalysts can be used. Such acid is added in a catalytic quantity, which is effectively 0.1 to 20 mole percent (related to the amount of diketene used).

The reaction can be carried out without the presence of any solvent, however, it is preferably conducted in a solvent, which is preferably an organic solvent.

Effective solvents include aromatic hydrocarbons and chlorinated aliphatic hydrocarbons. Examples of useful aromatic hydrocarbon solvents are benzene and toluene.

Examples of the chlorinated aliphatic hydrocarbon solvents are carbon tetrachloride, ethyl chloride, 1,1-dichloroethane, 1,2-dichloroethane, 1,1,2,2-tetrachloroethane, 1,1,2-trichloroethane, 1,1,1-trichloroethane, propyl chloride, isopropyl chloride, 2,2-dichloropropane, 1,2,3-trichloropropane, butyl chloride and isobutyl chloride. The preferred solvent is methylene chloride. Other organic solvents include acetone, methylethyl ketene, acetamide, ethanol, methanol, isopropyl alcohol, n-butyl alcohol, benzaldehyde, cyclohexane, glycerol and dimethyl sulfoxide. Effectively, 200 to 1000 grams of the solvent is used per mole of diketene. The same solvent can be used in all three reaction steps of the process, or a different solvent can be used in one or more of the reaction steps. The solvent has to be liquid in at least part of the temperature range of +30° (or +50°) to −40° C.

The mole ratio of HCl to diketene in the first step can vary widely. Effectively, 1.1 to 10 moles, and preferably 1.95 to 6.5 moles, of HCl is used per mole of diketene.

For the chlorination with chlorine in the second step, preferably 0.9 to 1.1 mole of chlorine is used per mole of acetoacetic acid chloride.

The 2-chloroacetoacetic acid chloride obtained in the second stage is converted with an amine having the formula HNRR' into the desired acid amide. The compound HNRR' can be ammonia, a primary or a secondary amine. Examples of specific primary amines are methylamine, ethylamine, propylamine, isopropylamine, methoxypropylamine, aniline, 4-Cl-aniline, 4-methoxyaniline, benzyl amine and phenyl ethyl amine. Examples of specific secondary amines are dimethylamine, diethylamine, methyl ethylamine, dipropylamine, butyl ethylamine, secondary butyl ethylamine, methyl isopropylamine, allyl methylamine, diethyl amine, N-benzyl aniline, N-benzyl-p-toluidine, N-benzyl-o-toluidine and N-benzyl-m-toluidine.

The alkyl, substituted alkyl, aryl, substituted aryl, alkaryl, substituted alkaryl, alkoxyaryl, substituted alkoxyaryl, alkoxyalkyl and substituted alkoxyalkyl groups of R and R' can each have 1 to 20 carbon atoms and most effectively have 1 to 8 carbon atoms.

Examples of alkyl groups which R and R' can be are methyl, ethyl, isobutyl, tertiary butyl, amyl, 2-hexyl isoamyl, 2-pentyl, 2-methyl-1-pentyl, n-heptyl, propyl, isopropyl, butyl, 2-methyl-1-butyl, 3-pentyl, 2-methyl-2-butyl, isohexyl, n-decyl, 3-methyl-1-pentyl, n-octyl, n-hexyl, 3-hexyl, 2,2-dimethyl-1-butyl, 2-ethyl-1-butyl, 4-methyl-1-hexyl, 2-methyl-1-pentyl, 2-octyl, n-dodecyl, 2,4-dimethyl-1-pentyl, n-nonyl, n-tetradecyl, n-nonadecyl, n-pentadecyl and n-heptadecyl. Examples of substituted alkyl groups which R and R' can be are those substituted with halogen (Cl, Br, I and F), cycloalkane groups, and nitro groups and mercapto groups, such as, 2-bromoethyl, 2-cyclohexyl, 2-cyclopentyl, 2,2-dichloroethyl, 2-chloroethyl, 2-iodoethyl, 2-fluoroethyl, 2-nitroethyl, 2-isobutyl, 2,2,2-trichloroethyl, 1,2-dichloropropyl, 1-nitro-1-chloropropyl, 1-bromo-1-fluoropropyl, 4-chlorobutyl and 5-chloro-1-pentyl. Examples of aryl groups which R and R' can be are benzyl, naphthyl, biphenyl, terphenyl, anthracenyl and phananthracenyl. Examples of substituted aryl groups which R and R' can be are alpha-chloronaphthyl, beta-bromonaphthyl, beta-nitronaphthyl, 9-chloroanthracenyl, 9,10-dichloroanthracenyl, 9-bromophenanthracenyl, 2-bromobenzyl, 2-chlorobenzyl, 2-nitrobenzyl, 4-nitrobenzyl and 2,3-dichlorobenzyl. Examples of alkaryl groups which R and R' can be are alphamethylnaphthyl, beta-methylnaphthyl, o-tolyl, m-tolyl, p-tolyl and 2-nitrobenzyl. Examples of substituted alkylaryl which R and R' can be are 2-(2-bromoethyl)benzyl, 4-(2-chloroethyl)benzyl, 2-chloromethylbenzyl, 2-nitromethylbenzyl and 2-iodomethylbenzyl. Examples of alkoxyaryl groups which R and R' can be are 2-methoxybenzyl, 4-methoxybenzyl and 2,4-diethoxybenzyl. Examples of substituted alkoxyaryl groups which R and R' can be are 2-(2-chloroethoxy)benzyl and 4-(2-bromoethoxy)benzyl. Examples of alkoxyalkyl groups which R and R' can be are 2-butoxyethyl, 2,2-diethoxyethyl, 2-ethoxyethyl, 2-propoxyethyl, 2-hexoxyethyl and 2-phenoxyethyl. Examples of substituted alkoxyalkyl groups which R and R' can be are chloromethoxyethyl and 2-chloroethoxy propyl.

A particularly preferred embodiment of this invention is where the three reaction steps are carried out in the same reaction medium and reaction vessel without there being any separating out of any of the intermediate products. An alcohol should not be used in the third reaction step.

By way of summary, this invention involves the production of 2-chloroacetoacetic acid amides by chlorination of acetoacetic acid chloride with chlorine and subsequent reaction with amines. Preferably the hydrochlorination is carried out in the presence of an acid catalyst. Preferably the methylene chloride is used as a solvent. Also, preferably the subject three-step reaction is carried out without isolation of the intermediate products.

As used herein, all percentages, parts, ratios and proportions are on a weight basis unless otherwise stated herein or otherwise obvious herefrom to one ordinarily skilled in the art.

EXAMPLE 1

Production of 2-chloroacetoacetic acid anilide:

In a double jacketed flask of 1000 ml size, equipped with a compressed air stirrer, thermometer, gas introducing tube with sintered glass plug, reflux cooler and cryomat, 50.4 g of diketene dissolved in methylene chloride (300 ml) was introduced and was cooled to −30° C. After the addition of 0.07 g (3 drops) of concentrated sulfuric acid, 48.5 g of hydrochloric acid was introduced into this solution during a 65 minute period at −30° to −20° C. Following such and after a reaction time of at least 1 hour, 43.0 g of chlorine was introduced over 40 minutes at −25° to −22° C. The hydrogen chloride formed at 20 torr was sucked off after ½ hour removed under reduced pressure.

Then, over a 46 minutes period and at −22° to −8° C., 110.8 g of aniline solved in 130.0 g of methylene chloride was added to this solution drop by drop. The resulting suspension, which was difficult to stir, was allowed to warm up to ambient temperature and was then stirred with 200.0 g of water. Half of the methylene chloride was distilled from the resulting 2-phase mixture on the rotavapor. The resulting white, solid product was filtered off, was washed three times with 30 ml portions of methylene chloride and was dried at 60° C. in the vacuum drying cabinet for 4 hours.

Yield: 100.3 g (which equals 79.0 percent, related to the diketene).

The two phases of the remaining filtrate were separated and the methylene chloride phase was evaporated to dryness on the rotavapor. In this manner 26.6 g of a brown product was obtained; by recrystallization from ethanol 6.0 g of a product (=4.7 percent, related to the diketene) were obtained from such product.

Total yield: 106.3 g (which equals 84.4 percent, based on the diketene) of 2-chloroacetoacetic acid anilide.

EXAMPLE 2

Production of 2-chloroacetoacetic acid-4'-chloroanilide:

To a solution of 2-chloroacetoacetic acid chloride (prepared analogously to Example 1, from 0.3 mole of diketene in 200 ml of methylene chloride) 76.6 g of 4-chloroaniline (0.6 mole) dissolved in 200 ml of methylene chloride was added drop by drop over 15 minutes at a temperature between −30° and −10° C. After 2 hours and after the temperature had risen to 10° C., 200 ml of water was added and the resultant methylene chloride phase was concentrated on the rotavapor to two-third of its original volume. The slightly grayish product obtained was filtered off and dried. This resulted in a crude yield of 63.3 g (which equals a 84.4 percent yield, based on the diketene).

EXAMPLE 3

Production of 2-chloroacetoacetic acid-4'-methoxyanilide:

73.9 g of 4-methoxyaniline (0.6 mole) dissolved in 200 ml of methylene chloride, was added drop by drop to a solution of 2-chloroacetoacetic acid chloride (prepared analogously to Example 1, from 0.3 mole to diketene) over 15 minutes at a temperature between −30° and −10° C. The material was processed further as described in Example 2.

A yield of 58.5 g of a slightly brownish product (which equals a 80.7 percent yield, related to the diketene) was obtained.

EXAMPLE 4

Production of 2-chloroacetoacetic acid benzyl amide:

Analogously to the Examples 2 and 3, 64.3 g of benzyl amine (0.6 mole) was reacted and 65.5 of a white product (which equals 96.7 percent yield, related to the diketene) was obtained.

EXAMPLE 5

Production of 2-chloroacetoacetic acid-2'-phenylethyl amide:

Analogously to Example 2 and 3, 72.7 g of 2-phenylethyl amine (0.6 mole) was reacted and 63.0 g of slightly yellowish crystals (which equals a 87.6 percent yield, related to the diketene) was obtained.

EXAMPLE 6

Production of 2-chloroacetoacetic acid isopropyl amide:

Analogously to Example 2 and 3, 35.5 g of ispropyl amine (0.6 mole) was reacted and 47.3 g of slightly brownish crystals (which equals 88.8 percent yield, related to the diketene) was obtained.

EXAMPLE 7

Production of 2-chloroacetoacetic acid-tert.butyl amide:

Analogously to Example 2 and 3, 43.9 g of tertiary butyl amine (0.6 mole) was reacted and 51.3 g of slightly brownish crystals (which equals 89.2 percent yield, related to the diketene) was obtained.

EXAMPLE 8

Production of 2-chloroacetoacetic acid-3'-methoxypropyl amide:

Analogously to Example 2 and 3, 53.5 g of 3-methoxypropyl amine (0.6 mole) was reacted and 57.8 g of a slightly brownish, viscous liquid, which was purified by distillation (which equals 92.8 percent yield, related to the diketene) was obtained.

EXAMPLE 9

Production of 2-chloroacetoacetic acid dimethyl amide:

Analogously to Example 2 and 3, 27.05 g of dimethyl amine (0.6 mole) was reacted and 41.2 of a viscous liquid, purified by distillation (which equals a 83.9 percent yield, related to diketene) was obtained.

EXAMPLE 10

Production of 2-chloroacetoacetic acid monomethyl amide:

Analogously to Example 2 and 3, 2-chloroacetoacetic acid chloride (produced from 0.6 mole of diketene in 400 ml of methylene chloride) and 37.3 g of methyl amine (1.2 mole) were reacted and 75.1 g of a purified product (which equals a 83.6 percent yield, related to diketene) was obtained through recrystallization from water.

EXAMPLE 11

Production of 2-chloroacetoacetic acid amide:

Analogously to Example 2 and 3, 2-chloroacetoacetic acid chloride (produced from 0.6 mole of diketene) was reaction with 20.5 g of ammonia (1.2 mole). 49.1 g of a product, purified by recrystallization from diisopropyl ether (which equals a 60.4 percent yield, related to diketene) was obtained.

EXAMPLE 12

Production of 2-chloroacetoacetic acid anilide:

Analogously to Example 1, 50.4 g of diketene was dissolved in 300 ml of methylene chloride and the solution was heated to 22° C. while being stirred. Subsequently, 0.14 g of $H_2SO_4$ was added by transfer with a pipet and then 48 g of HCl of gas was conducted through the solution at 30° C. within 60 minutes. After 30 minutes, 43 g of chlorine gas was introduced over 40 minutes at a temperature of 30° C. Subsequently, the solution was mixed during 20 minutes at 30° C. with 111 g of aniline and the solution was stirred for another 2 hours. Then the solution was cooled to 10° C. and was stirred with water for 2 hours. Then the solution was filtered. The filter cake was washed with 10 ml of methylene chloride and was dried. 49.4 g of a white product, having a melting point of 136° to 137° C., corresponding to a yield of 39.2 percent, was obtained.

The organic phase of the filtrate was concentrated and an additional 59.6 g of the raw product was obtained (this corresponded to a yield of 21 percent with a purity of 44.5 percent).

EXAMPLE 13

Production of 2-chloroacetoacetic acid anilide:

Analogously to Example 12, the HCl addition, chlorination and amidation with aniline were carried out at 10° C. After processing in the same manner, 58.0 g of product, having a melting point of 136° to 138° C., corresponding to a yield of 46.0 percent, was obtained. After concentration of the organic phase of the filtrate, an additional 64.2 g of the raw product (that corresponds to a yield of 21.9 percent with a purity of 43.7 percent) was obtained.

EXAMPLE 14

Production of 2-chloroacetoacetic acid anilide:

In an apparatus as in Example 1, 50.4 g of diketene (dissolved in 100 ml of methylene chloride) was added and was cooled to −10° C. Over 60 minutes, 48 g of hydrochloric acid was introduced at −10° C. The solution was subsequently stirred over a 30 minute period. Then the reaction mixture was cooled to −20° C. and 41 g of chlorine gas was introduced during 1 hour at this temperature. The solution was subsequently heated to 10° C. and the hydrogen chloride which developed was removed under vacuum. 400 ml of toluene was added to the solution. Then 111 g of aniline was added drop by drop during 40 minutes. The suspension was stirred for an additional 2 hours. 200 ml of water were added and the suspension was stirred for 15 minutes. The suspension was then filtered. The cake was washed with 100 ml of water and 60 ml of toluene, and was subsequently dried. 102.7 g of product was obtained, having a melting point of 134° to 135° C., corresponding to a yield by weight of 81.4 percent. After concentration, the organic phase of the filtrate produced a sticky residue (20.6 g).

What is claimed is:

1. Process for the production of a 2-chloroacetoacetic acid amide comprising (a) converting diketene at a temperature of +30° to −40° C. with the help of hydrogen chloride into acetoacetic acid chloride, (b) introducing chlorine at a temperature of +30° to −40° C. into the acetoacetic acid chloride, whereby 2-chloroacetoacetic acid chloride forms, and (c) converting the 2-chloroacetoacetic acid chloride into the corresponding amide at a temperature of +50° to −40° C. by reaction with a N-compound having the formula:

wherein (i) R and R' are H, or (ii) R and R' are the same or different alkyl, substituted alkyl, aryl, substituted aryl, alkyl aryl, substituted alkyl aryl, alkoxy aryl, substituted alkoxy aryl, alkoxy alkyl or substituted alkoxy alkyl, or (iii) R is H, and R' is alkyl, substituted alkyl, aryl, substituted aryl, alkyl aryl, substituted alkyl aryl, alkoxy aryl, substituted alkoxy aryl, alkoxy alkyl or substituted alkoxy alkyl.

2. Process as claimed in claim 1 wherein, concerning R and/or R', the alkyl, substituted alkyl, aryl, substituted aryl, alkylaryl, substituted alkylaryl, alkoxyaryl, substituted alkoxyaryl, alkoxyaryl or substituted alkoxyalkyl each has 1 to 20 carbon atoms.

3. Process as claimed in claim 1 or 2 wherein the chlorination in step (a) and step (b) is carried out in the presence of an acid catalyst.

4. Process as claimed in claim 3 wherein the acid catalyst is present in an amount of 0.1 to 20 mole percent, based on the amount of diketene.

5. Process as claimed in claim 4 wherein the acid catalyst is a Lewis acid, an inorganic acid or a strong carboxylic acid.

6. Process as claimed in claim 3 wherein the chlorination is carried out in an organic solvent.

7. Process as claimed in claim 1 wherein one or more of steps (a), (b) and (c) are conducted in the presence of a solvent.

8. Process as claimed in claim 7 wherein the solvent is an aromatic hydrocarbon or a chlorinated aliphatic hydrocarbon.

9. Process as claimed in claim 1 wherein the same chlorinated aliphatic hydrocarbon solvent is used in all three of the reaction steps.

10. Process as claimed in claim 9 wherein the chlorinated aliphatic hydrocarbon solvent is methylene chloride.

11. Process as claimed in claim 10 wherein the chlorinated aliphatic hydrocarbon is used in an amount of 200 to 1000 grams per mole of diketene.

12. Process as claimed in claim 1 wherein, in step (a), the molar ratio of HCl to diketene is 1.1 to 10 moles of HCl per mole of diketene.

13. Process as claimed in claim 1 wherein, in step (a), the molar ratio of HCl to diketene is 1.95 to 6.5 moles of HCl per mole of diketene.

14. Process as claimed in claim 1 wherein, in step (b), 0.9 to 1.1 mole of chlorine is used per mole of acetoacetic acid chloride.

15. Process as claimed in claim 1 wherein the three-step reaction is carried out without isolation of the intermediate products.

16. Composition comprising 2-chloroacetoacetic acid chloride and a N-compound having the formula:

wherein (i) R and R' are H, or (ii) R and R' are the same or different alkyl, substituted alkyl, aryl, substituted aryl, alkyl aryl, substituted alkyl aryl, alkoxy aryl, substituted alkoxy aryl, alkoxy alkyl or substituted alkoxy alkyl, or (iii) R is H, and R' is alkyl, substituted alkyl, aryl, substituted aryl, alkyl aryl, substituted alkyl aryl, alkoxy alkyl, substituted alkoxy aryl, alkoxy alkyl or substituted alkoxy alkyl.

17. Composition as claimed in claim 16 wherein, concerning R and/or R', the alkyl, substituted alkyl, aryl, substituted aryl, alkylaryl, substituted alkylaryl, alkoxyaryl, substituted alkoxyaryl, alkoxyalkyl or substituted alkoxyalkyl each has 1 to 20 carbon atoms.

18. Composition as claimed in claim 16 wherein a solvent which is an aromatic hydrocarbon or a chlorinated aliphatic hydrocarbon is present.

19. Composition as claimed in claim 18 wherein the chlorinated aliphatic hydrocarbon solvent is methylene chloride.

20. Composition as claimed in claim 18 wherein a Lewis acid catalyst is also present.

21. Process for the production of a 2-chloroacetoacetic acid amide consisting essentially of:
(a) converting diketene at a temperature of +30° to −40° C. with the help of hydrogen chloride in the presence of a solvent into acetoacetic acid chloride, the molar ratio of HCl to diketene being 1.1 to 10 moles of HCl per mole of diketene, and the solvent being an aromatic hydrocarbon or a chlorinated aliphatic hydrocarbon;
(b) introducing chlorine at a temperature of +30° to −40° C. into the acetoacetic acid chloride in the presence of a solvent, whereby 2-chloracetoacetic acid chloride forms, the chlorination being carried out in the presence of an acid catalyst, the acid catalyst being present in an amount of 0.1 to 20 mole percent, based on the amount of diketene, 0.9 to 1.1 mole of chlorine being used per mole of acetoacetic acid chloride, and the solvent being an aromatic hydrocarbon or a chlorinated aliphatic hydrocarbon; and
(c) converting the 2-chloroacetoacetic acid chloride into the corresponding amide at a temperature of +50° to −40° C. by reaction in the presence of a solvent with a N-compound having the formula:

wherein (i) R and R' are H, or (ii) R and R' are the same or different alkyl, substituted alkyl, aryl, substituted aryl, alkyl aryl, substituted alkyl aryl, alkoxy aryl, substituted alkoxy alkyl, alkoxy alkyl or substituted alkoxy alkyl, or (iii) R is H, and R' is alkyl, substituted alkyl, aryl, substituted aryl, alkyl aryl, substituted alkyl aryl, alkoxy alkyl, substituted alkoxy aryl, alkoxy alkyl or substituted alkoxy alkyl, concerning R and/or R', the alkyl, substituted alkyl, aryl, substituted aryl, alkylaryl, substituted alkylaryl, alkoxyaryl, substituted alkoxyaryl, alkoxyalkyl or substituted alkoxyalkyl each has 1 to 20 carbon atoms, and the chlorination being carried out in the presence of an acid catalyst, steps (a), (b) and (c) hereof being conducted without isolation of the intermediate products.

* * * * *